(12) United States Patent
Pierart

(10) Patent No.: US 12,029,585 B2
(45) Date of Patent: Jul. 9, 2024

(54) BI-RIGIDITY ADHESIVE PATCH

(71) Applicant: PKvitality, Paris (FR)

(72) Inventor: Luc Pierart, Villejuif (FR)

(73) Assignee: PKvitality, Paris (FR)

( * ) Notice: Subject to any disclaimer, the term of this patent is extended or adjusted under 35 U.S.C. 154(b) by 740 days.

(21) Appl. No.: 17/265,421

(22) PCT Filed: Aug. 2, 2019

(86) PCT No.: PCT/EP2019/070948
§ 371 (c)(1),
(2) Date: Feb. 2, 2021

(87) PCT Pub. No.: WO2020/025823
PCT Pub. Date: Feb. 6, 2020

(65) Prior Publication Data
US 2021/0298679 A1 Sep. 30, 2021

(30) Foreign Application Priority Data
Aug. 3, 2018 (EP) ..................................... 18306070

(51) Int. Cl.
*A61B 5/00* (2006.01)
*A61B 5/145* (2006.01)
(52) U.S. Cl.
CPC ........ *A61B 5/6833* (2013.01); *A61B 5/14514* (2013.01); *A61B 5/6831* (2013.01); *A61B 2560/0443* (2013.01)
(58) Field of Classification Search
CPC . A61B 5/6833; A61B 5/14514; A61B 5/6831; A61B 2560/0443; A61B 5/157;
(Continued)

(56) References Cited

U.S. PATENT DOCUMENTS

| | | | |
|---|---|---|---|
| 6,925,317 B1* | 8/2005 | Samuels | .............. A61B 5/6833 600/344 |
| 2011/0105872 A1* | 5/2011 | Chickering, III | .. A61B 5/14514 600/573 |
| 2017/0239457 A1 | 8/2017 | Asai et al. | |

FOREIGN PATENT DOCUMENTS

| | | |
|---|---|---|
| EP | 2298177 A2 | 3/2011 |
| EP | 2298177 A3 | 12/2012 |
| EP | 2901929 A1 | 8/2015 |

OTHER PUBLICATIONS

International Search Report dated Sep. 19, 2019 in Application No. PCT/EP2019/070948.

(Continued)

*Primary Examiner* — Eric F Winakur
*Assistant Examiner* — Abid A Mustansir
(74) *Attorney, Agent, or Firm* — Sughrue Mion, PLLC

(57) ABSTRACT

An assembly having a patch (250) for a body-monitoring system, the patch having a main body (251) with an opening (252) of at least 2 mm diameter, the main body having a rigid zone (256) around the opening and a flexible zone (258) on either side of the rigid zone and preferably all around the rigid zone, and a capsule (220), the capsule being configured to be placed in the opening of the patch and to be rigidly attached to same. The capsule has microneedles (210) configured to be inserted in the skin in order to sample or analyse a bodily fluid of the wearer of a body-monitoring system when the system is positioned on a limb of a user, the rigid zone of the capsule enabling a transmission of the forces received by the patch to the capsule.

19 Claims, 4 Drawing Sheets

Figure 1:
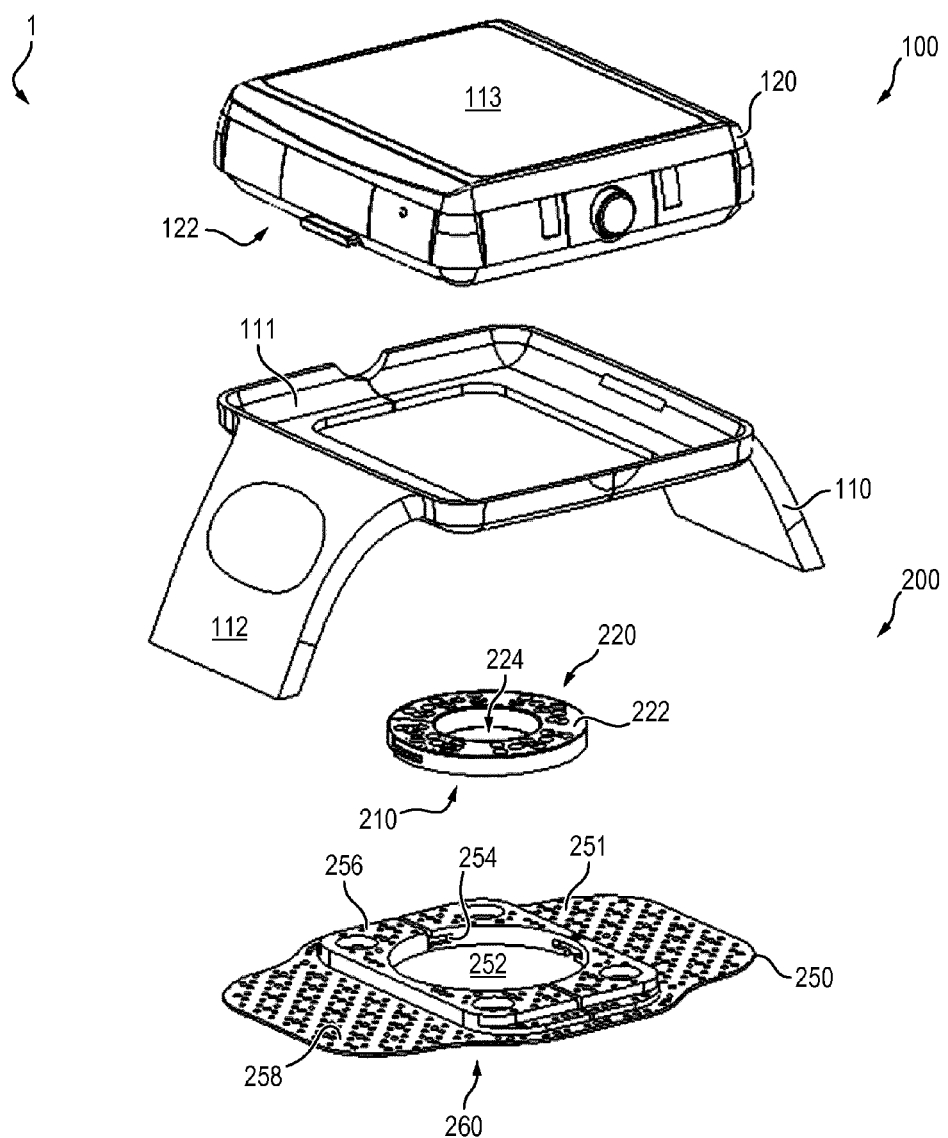

(58) Field of Classification Search
CPC ........ A61B 5/150984; A61B 5/150969; A61B 5/150267; A61B 5/14532; A61B 5/150022; A61B 5/681; A61B 5/685
See application file for complete search history.

(56) References Cited

OTHER PUBLICATIONS

Written Opinion of the International Searching Authority dated Sep. 19, 2019 in Application No. PCT/EP2019/070948.
European Search Report dated Feb. 11, 2019 in Application No. 18306070.6.

* cited by examiner

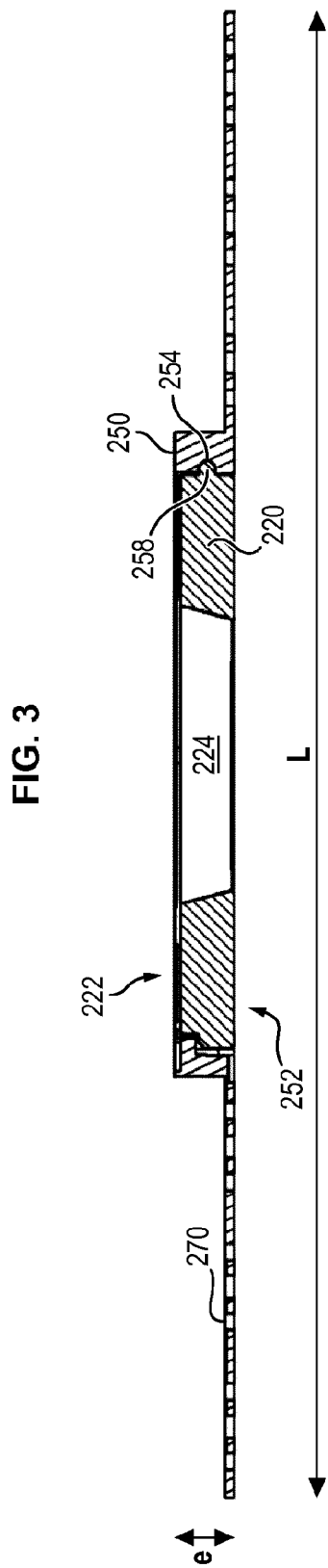

BI-RIGIDITY ADHESIVE PATCH

CROSS REFERENCE TO RELATED APPLICATIONS

This application is a National Stage of International Application No. PCT/EP2019/070948 filed Aug. 2, 2019, claiming priority based on European Patent Application No. 18306070.6 filed Aug. 3, 2018.

GENERAL TECHNICAL FIELD

The present invention relates to a body monitoring system via body, typically interstitial, fluid analysis using microneedles.

More specifically, the present invention concerns a patch for the management of the holding of the microneedles in the skin.

STATE OF THE ART

Some pathologies such as diabetes require daily monitoring of biochemical parameters of the human body, i.e. concentrations of some compounds (glycemia in the example of glucose).

To this end, it is common to prick a point of the skin so as to bead up a drop of blood, and to analyze this drop either reactively (for example with a strip) or electronically (for example by at least one analytical sensor), so as to estimate the target parameter(s).

Much less invasive advanced systems are known today, which simply analyze the interstitial fluid, that is to say, the fluid that fills the space between blood capillaries and cells. It has indeed an ionic composition close to that of blood plasma.

These advanced systems thus allow monitoring the desired biochemical parameters transcutaneously that is to say without the need to evenly pierce the skin and take samples.

Devices with microneedles are known, which have the advantage of being less invasive than conventional needles. However, it is important that these microneedles remain in place.

There are for that purpose indwelling devices where microneedles are held on the skin with an adhesive tape. However, it is desirable to be able to carry out a continuous or quasi-continuous control, which requires autonomous devices. The GlucoWatch device, which used iontophoresis (and not needles) can be cited.

The device is also known from document WO2018104647, which has a casing comprising a removable capsule, the capsule accommodating microneedles configured to sample interstitial fluid. The casing, for its part, accommodates most part of the electronics.

This portable device, typically on the wrist, allows continuous measurement and it suffices to change the capsule in order to change microneedles.

However, when such a device is worn on the wrist, the difficulty lies in reconciling a system that allows holding the microneedles in position in the skin and a replaceable system.

In addition, it is important that the device is easy to use. The invention will overcome these difficulties.

PRESENTATION OF THE INVENTION

In order to address some of these issues, the invention proposes a set for a body monitoring system, comprising:

a patch for a body monitoring system, the patch comprising a main body with an orifice of at least 2 mm in diameter, the main body comprising a rigid area around the orifice and a flexible area on either side of the rigid area and preferably all around the rigid area, and a capsule configured to be placed in the opening of the patch and to be secured thereto, the capsule comprising microneedles configured to be inserted into the skin to sample or analyze a body fluid from the wearer of a body monitoring system when the latter is positioned on a limb of a user, the rigid area of the main body allowing a transmission of the forces received by the patch to the capsule.

In one embodiment, the rigid area has a divisibility line interrupted by the orifice, the divisibility line being configured to allow folding the rigid area of the patch.

In one embodiment, the divisibility line is an axis of symmetry of the orifice.

In one embodiment, the orifice comprises on an inner wall, a groove or point recesses, configured to receive a capsule.

In one embodiment, the rigid area has a Shore hardness greater than the flexible area, for example a Shore hardness comprised between 20 and 40 for the flexible area and a Shore hardness comprised between 60 and 80 for the rigid area.

In one embodiment, the material of the rigid area is harder than the material of the flexible area, the two materials being different.

In one embodiment, the rigid area is at least twice as thick as the flexible area, preferably at least three times as thick.

In one embodiment, the patch comprises a planar adhesive substantially covering a planar face of the rigid and flexible areas.

In one embodiment, the adhesive is either a silicone-based or an acrylic-based adhesive.

In one embodiment, the main body, preferably the flexible area, comprises a plurality of through openings.

In one embodiment, the main body, preferably the flexible area, comprises a plurality of through openings, and the adhesive comprises a plurality of through openings, the size of the openings of the main body being larger than the size of the openings of the adhesive, and/or the opening area density of the main body is greater than the opening area density of the adhesive, and/or the opening density of the main body is greater than the opening density of the adhesive.

In one embodiment, the openings of the main body are skewed.

In one embodiment, the rigid area comprises a step having a thickness less than the thickness of the rest of the rigid area.

In one embodiment, the capsule has a thickness identical to the thickness of the rigid area of the main body of the patch.

The invention also proposes a body monitoring system, intended to be attached to a limb, comprising:
an assembly as defined above,
a casing, able to be coupled with the capsule, inside which there is a battery and a processor, the processor being configured to process data obtained using the sample or the measurement taken by the microneedles,
a strap, configured to hold the casing in place on the limb, in which the capsule is positioned within the central orifice of the patch.

In one embodiment, the strap or the casing is in contact with the rigid area of the patch, to transmit the forces of the strap to the patch, in order to maintain the penetration of the needles by means of the capsule attached to the rigid area of the main body of the patch, in particular by means of the steps defined above.

The invention proposes a kit comprising a plurality of patches as defined above, in which all the patches are identical or at least two patches have:
a different length, and/or
a different width, and/or
a different orifice shape,
where appropriate, a different adhesive

PRESENTATION OF THE FIGURES

Figure 2A:
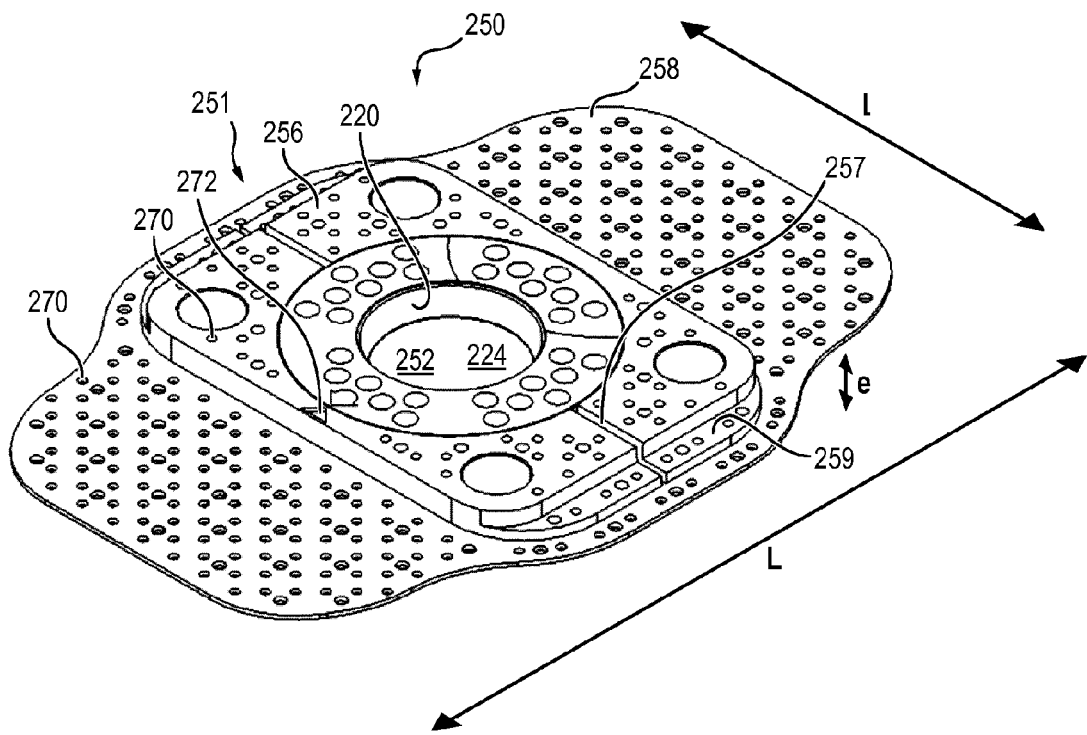
Figure 2B:
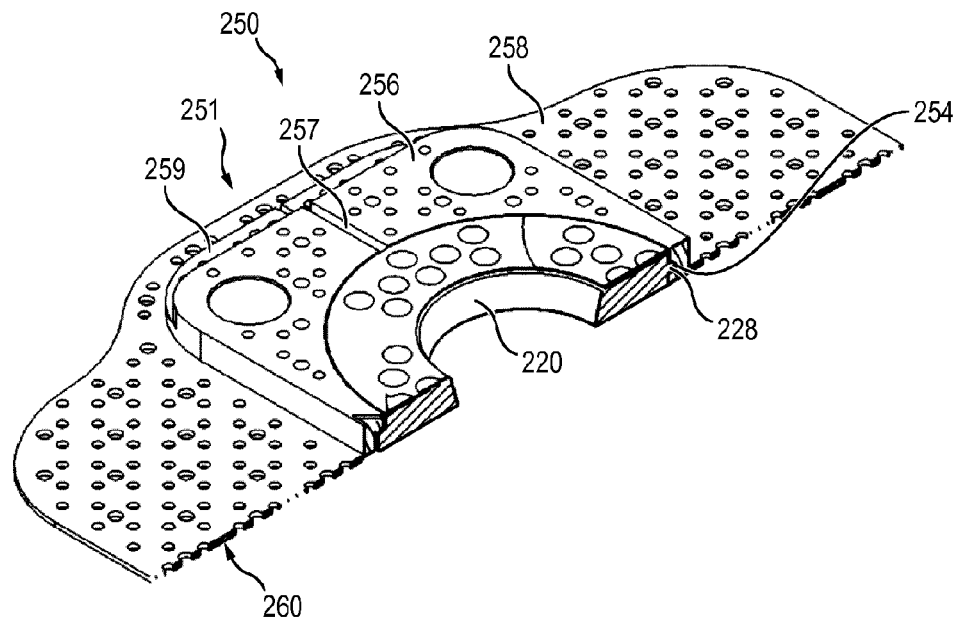
Figure 4:
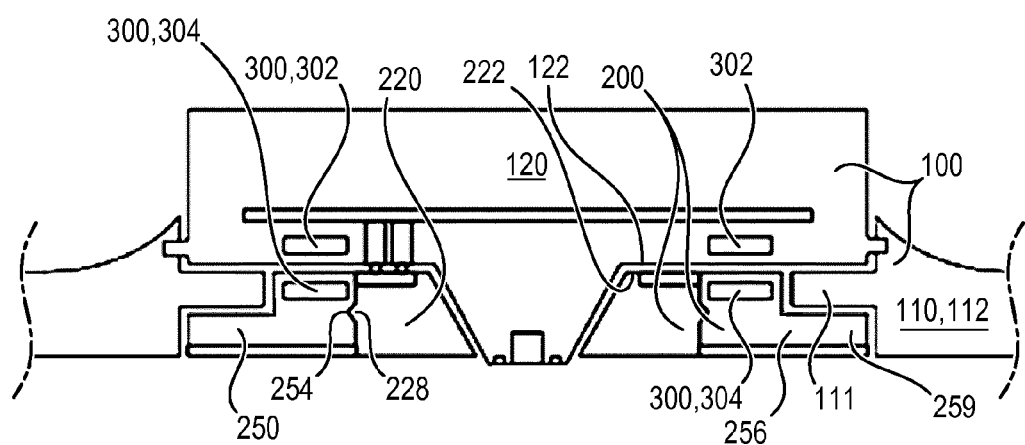

Other characteristics and advantages of the present invention will become apparent upon reading the following description of a preferred embodiment. This description will be given with reference to the appended drawings in which:

FIG. 1 illustrates an exploded view of a bracelet, a casing, a capsule and a patch as usable in the framework of the invention, FIGS. 2a and 2b illustrate a three-dimensional full and cut view of a patch and of a capsule attached to the patch, FIG. 3 illustrates a sectional view of FIGS. 2a and 2b, FIG. 4 illustrates the arrangement of the different modules that form the system (dimensions different from the dimensions of FIGS. 2a and 2b).

DETAILED DESCRIPTION

General Architecture

With reference to FIGS. 1 to 4, the present invention concerns an electronic body monitoring system 1. It is an improvement in the device from document WO2018104647. Consequently, the invention falls within the same general concept of an autonomous integral system with low pain and low hygiene risk which is reusable.

By "body monitoring" is meant the verification of biochemical constants of a person wearing the system 1, typically the concentration of a protein, a hormone, a marker, oxygen, nutrients, etc., in the interstitial fluid of the person. The example of glycemia can be cited. Those skilled in the art will be able, if necessary, to monitor other physical body quantities such as lactate, hydration etc.

The description will be illustrated with interstitial fluid but applies to the other body fluids such as blood.

The system 1 is said to be autonomous because it does not require the use of additional equipment.

The system 1 is intended to be attached to a limb of a living being, typically an arm or a leg of a human being. The preferred attachment area is the wrist where the system 1 is similar to a watch.

The system 1 is formed of two modules 100, 200 (FIG. 1) interconnected by a separable link 300 which is reusable. A coupled position and a free position are thus defined. In the coupled position, the two modules 100, 200 are not physically separated and can exchange data.

The first module 100 comprises in particular means for attaching and tightening 110 the system 1 to a limb (called strap 112 or bracelet) and the second module 200 comprises a capsule 220 that integrates microneedles 210 configured to be inserted into the skin (in a superficial part of the epidermis). These microneedles 210, when the first module 100 is in position on the limb, allow sampling and/or analyzing a body fluid, as mentioned above.

The microneedles advantageously consist of an array of microneedles 210 in contact with the skin when the capsule 220 is placed on the body of a person. The microneedles 210 can therefore be either hollow, to sample fluid, or full, to analyze the fluid directly. In the first case, typically, the microneedles 210 allow the extraction of interstitial fluid from the dermis painlessly without beading up blood, and send it to a sensor in the system 1 (more specifically preferably in the second module 200). In the second case, the microneedles 210 do not sample any fluid and integrate the sensor on their surface, in the form of a biochemical material able to react with the analyte desired be measured in the fluid. In the case of pierced microneedles forming a channel in each microneedle, a sample can be taken by fluidly connecting a system for pumping the interstitial fluid to the channel, or simply by capillarity. An analysis system may comprise microneedles each provided with an electrode or a set of electrodes, or be offset after the microneedles, so as to cause an electrochemical reaction adapted to detect an analyte in the interstitial fluid.

Preferably, said microneedles comprise between four and fifty, substantially pyramidal, microneedles with tips of a height comprised between 100 µm and 1,000 µm, preferably 0.3 mm and 0.8 mm. Each of these advantageous characteristics of the microneedles 210 can be taken separately or in combination with the other ones.

The two modules 100 and 200 each have a coupling face 122, 222, of complementary shape, which allows placing the second module 200 in a location for accommodating the first module 100.

Finally, the first module 100 and the second module 200 are configured to be coupled by a separable link 300.

As illustrated in FIGS. 1 and 4, the first module 100 further comprises a casing 120 in which are disposed data processing means (particularly a processor or a microcontroller) configured to process measurements acquired by the sensor, and where appropriate, data storage means (in particular a memory, particularly of the flash type, and/or the memory of the microcontroller) allowing for example storing these measurements, and/or a date of the first use of each sensor to calculate an expiry date of the sensor(s) (the biochemical sensors have a limited lifespan). The data processing means are also used to generate instructions towards different components. In the framework of this description, these different functions are performed by the same unit. However, it is possible to provide for dedicated processors. The system also comprises a battery, advantageously a rechargeable battery, for the electrical supply to the components, for example via a port (understood as also being able to be used to connect the system 1, for example to a computer for downloading the acquired and/or processed data).

Preferably, the system 1 can comprise wireless connection means (particularly of the WiFi but also Bluetooth or even 3G/4G type) for a connection to a network, particularly the Internet, and a user interface such as a screen 113, possibly touch screen to display the monitoring results to the user.

Those skilled in the art are familiar with algorithms for processing sensor measurements 24 and the associated interfaces, and will know how to implement them in the present system 1.

The casing 120 further comprises electrical connectors, on its coupling face 122, which couples with the coupling face 222 of the capsule 220.

The capsule 220 of the second module 200 has the shape of a closed, typically sealed, box which can be coupled with the casing 120. This capsule 220 is interchangeable, which allows obtaining an economical and efficient system, where only the parts said consumables need to be changed. The capsule 220 may have an annular shape, with a through opening 224 in the center. In a variant mentioned above, the sensor is positioned inside the capsule 220 (or in the casing 120) and analyzes the fluid sampled by the microneedles. The capsule 220 comprises electrical connectors 226, on a coupling face 222 with the casing 120, which can cooperate with the electrical connectors of the casing 120. If there is fluid transmission from the second to the first module, then complementary fluid connectors are provided on the capsule 220 and the casing 120.

Finally, the second module 200 comprises a patch 250, removably secured to the capsule 222, which is described in detail below.

The second module 200 (capsule 220 and patch 250) forms an interchangeable assembly of the system which is chosen according to the desired monitoring type and according to the state of deterioration of the microneedles 210 and/or of the sensor.

Indeed, insofar as the capsule 220 contains the microneedles 210 and/or the sensor (in particular in the case of microneedles that take a sample), changing the capsule 220 allows changing the equipment if it is at the end of its life or if it is desired to change the measured physical quantity, in a simple, fast and safe handling, without having to throw away other parts (particularly the first module 100).

Insofar as the capsule 220 minimizes the amount of expensive elements and/or materials (advanced electronic equipment such as a battery or wireless communication means), it is relatively inexpensive.

The Patch 250 (FIGS. 2a, 2b Et 3)

The patch 250 operates as an adhesive to maintain the penetration of the microneedles 210 into the skin. The capsule 220 being attached to the patch 250, it takes advantage of the patch-adhesive power 250 to be held against the skin.

The patch 250, inexpensive, can be changed more frequently than the capsule 220. This is made possible thanks to the removable fastening between the patch 250 and the capsule 220.

It is designed to look like a dressing, so that the persons wearing it don't feel stigmatized by wearing an unusual element.

The patch 250 has a length L comprised between 3 cm and 10 cm, a width I comprised between 3 cm and 10 cm and a thickness e comprised between 0.1 cm and 1 cm.

The patch 250 comprises a main body 251 with an orifice, called central orifice 252, configured to receive the capsule 220, and advantageously an adhesive 260 (if the material(s) of the patch do not already operate as an adhesive, for example). By "central" is meant that the central orifice 252 is integrally within the main body 251, and not on one edge. However, "central" does not necessarily mean "centered": it is possible that the central orifice 252 is not centered on the main body 251.

The orifice 252 is at least 2 mm in diameter (therefore it is not a micro-orifice that allows aerating the patch).

The main body 251 comprises two areas: a rigid area 256, which extends around the central orifice 252, and a flexible area 258, which extends at least on either side (preferably all around) of the rigid area 256. The flexible area 258 extends essentially along two opposite sides of the rigid area 256 in the lengthwise L direction, in order to conform to the curvature of the limb. But preferably, the flexible area 258 is all around the rigid area 256, with a greater length in the lengthwise L direction (between 1 and 3 cm for example) than in the widthwise direction (between 0.2 and 0.5 cm for example).

The rigid 256 and flexible 258 areas correspond to different portions of the patch.

The rigid area 256 is strong, hardly foldable during normal use with fingers. Conversely, the flexible area 258 is foldable without forcing, almost under its own weight.

The rigid 256 and flexible 258 areas do not have the same thickness. Preferably, the rigid area 256 is twice as thick, or even three times as thick as the flexible area 258. The flexible area 258 for its part is as fine as possible, for two reasons: the adhesion and the shock absorption.

Indeed, like a dressing, the flexibility allows conforming to the contour of the limb and particularly of the wrist, which ensures good adhesion.

In addition, to avoid involuntary tearing of the microneedles 210 from the skin, it is important that the tearing forces exerted on the patch 250 are not transmitted to the capsule 220. In this respect, the flexibility of the flexible area 258 ensures an absence of transmission of torque or force to the rigid area 256 and therefore to the capsule 220. The small thickness of the flexible area 258 also makes it invisible in use and therefore little likely to be torn by mistake.

Conversely, the rigid area 258 has the function of holding the capsule 220 in place and of transmitting thereto the holding forces it receives from the second module 200, which presses on the rigid area towards the skin.

The patch 250, with the rigid area and the flexible area, thus fulfills two important functions of the patch 250.

Seen from the side (FIG. 3), the patch 250 has a planar face, configured to be in contact with the skin, and a non-planar face, because of the rigid area 258, configured to be in contact with the first module 100.

The rigid area 256 has a shape, in the plane, similar to the shape of the casing 120, so that when the system 1 is worn, the rigid area 256 is masked by the casing 120 and the bracelet 110. In the Figures, this shape is rectangular with rounded corners.

The rigid 256 and flexible 258 areas are typically made of two materials (for example polymers) with different physical characteristics. The Shore hardness of the rigid area 256 is for example comprised between 40 and 60, while the Shore hardness of the flexible area 258 is for example comprised between 20 and 40. The difference in rigidity is obtained either by a different thickness or by a choice of different material or even by the same material with different properties or a mixture of these two criteria.

For example, the flexible area 258 is made of silicone and the rigid part is made in another plastic (insert).

For example the rigid area 256 is also made of more rigid silicone.

In one embodiment, a rigid part is added onto a flexible layer to form the rigid area. In another embodiment, the flexible layer is added around a rigid part.

The Patch 250 and the Capsule 220, Divisibility of the Patch 250

Around the opening 252, the thickness of the rigid area 256 is substantially equal (even equal) to the thickness of the capsule 220 (within more or less 5% of the thickness of the capsule 210). The flexible area is finer to be able to conform to the shape of the limb and also to cause the least discomfort to the user in his daily life. Indeed, in the case of a wrist, the capsule 220 is positioned on a rather flat region of the limb, while the flexible area 258 of the patch 250 extends up to the curvature of the wrist.

To secure the capsule 220 to the patch 250 (or vice versa), the central orifice 252 comprises, on its inner wall, a groove or point recesses 254. They operate as notches to receive a protrusion 228 on an external annular wall of the capsule 220. Preferably, the arrangement of the notches 254 and of the protrusions 228 is such that it prevents the rotation of the capsule 220 within the central orifice 252 of the patch 250. A preferred solution consists in providing one or more point notches, which block the rotation.

In addition, the rigidity of the rigid area 258 allows making the patch 250 divisible on either side of the central orifice 252, to facilitate the insertion of the capsule 220: it suffices to insert the capsule 220 against part of the central orifice 252, then unfold the patch 250 to be flattened again. In this regard, a suitable choice of material for the rigid area 256 may suffice, but there is a risk that the divisibility will not take place at the right place. To address this problem, the rigid area 256 comprises a divisibility line 257 which extends over the entire rigid area 256 (in the figures: in the widthwise I direction), by passing through the central orifice 252. This divisibility line 257 facilitates the rupture of the patch 250 for the insertion of the capsule 220, which facilitates the handling. Preferably, the divisibility line 257 corresponds to an axis of symmetry of the opening 252 (apart from the notches 258), which is generally an axis of symmetry of the rigid area 256 and of the main body 251. The divisibility line 257 is typically made by a groove on the surface of the rigid area 256.

As the capsule 220 is placed by folding the central orifice 252, the point recesses of the inner wall of the central orifice 252 are not disposed symmetrically with respect to the divisibility line 257: indeed, the patch 250 is placed by insertion on one half of the folded central orifice 252. Consequently, the disposition of the grooves or the point recesses is adapted accordingly.

The Patch 250 and the Strap/Bracelet 110

When the two modules 100, 200 are assembled, the casing 120 and the patch 250 are in contact with the rigid area 256 which is around the opening 252 (see FIG. 4). This allows a first force take-up towards the capsule 220, via the patch 250.

More specifically, according to the embodiment illustrated in FIGS. 1, 2a and 3, in order to also have the bracelet or the strap 210 which exerts a force on the patch 250 (to press it against the skin), the rigid area 256 comprises, at its lateral ends, a step 259 of the rigid area 256 which is manifested by a lesser thickness (but typically always greater than that of the flexible area 258). Complementarily, the bracelet 110 comprises, on each side (preferably on the four sides in the case of a rectangular shape or over the entire periphery in the case of a circular or oval shape), a tab 111 which is positioned above the step 259 (and under the casing 120). The tab 111 and the step 259 have a small width, of a few millimeters, but extend over an entire length of the rigid area 256.

In the present description, unless otherwise stated, references to the thickness of the rigid area 256 concern the thickness in the absence of a step. It is thus possible to define a main region of the rigid area 256, which has the maximum thickness (substantially equal to that of the capsule) and a secondary region of the rigid area 258, which corresponds to the step 259, which has a lesser thickness.

The force take-up by the bracelet 110 has two advantages: a first interest is that the force comes from the bracelet 110 itself, which is tightened on one's wrist or limb (direct transmission), and a second interest comes from the fact that the system 1 can be worn without the casing 120. Therefore, to hold the patch 250 properly, the force must be taken up by the bracelet 110 and not the casing 120.

Adhesive

The adhesive 260 is in the form of a planar layer, facing planar faces of the rigid 256 and flexible 254 areas, on the side intended to be on the skin.

The adhesive 260 used is advantageously a silicone-based adhesive for its ability to be peeled and stuck, for the slight irritations it causes, for better management during showers and the absence of marks on the skin. In addition, the silicone operates very well in lateral tearing and poorly in traction, but it is the bracelet/strap that performs this function. An acrylic-based adhesive can alternatively be used, which has stronger adhesive power than silicone but which is not peelable and stickable.

In order to protect the adhesive of the patch 250 (packaging, transport, etc.), the adhesive 260 can be covered with a layer of peel-off paper.

Breathability

In order to facilitate skin breathing and avoid maceration effects, the main body 251 comprises a plurality of through openings 270, both in the flexible area and in the rigid area. The openings have a diameter comprised between 0.1 and 2 mm. Likewise, the adhesive 260 comprises through openings (not shown in the figures) so that air communication is made from the skin.

In order to ensure that the openings of the adhesive 260 communicate with openings 270 of the main body 251, the density of the openings of the adhesive is greater than that of the openings 270 of the main body 251 and the size of the openings of the adhesive is smaller than that of the openings 270 of the main body 251. Thus, any superposition of the adhesive on the main body generates communication between the openings, without it being necessary to seek to align openings with each other.

Finally, for aesthetic reasons (absence of skin visibility when the patch is worn alone), the openings of the main body can be inclined (relative to a plane formed by the patch 250 when it is flattened).

Marker

Finally, the patch 250 comprises a distinctive sign 272 around the opening in order to be able to easily orient the capsule 220 in the patch 250. This distinctive sign is represented by an arrow 272 in the figures. Two arrows 272 may be provided, one on each side, depending on the direction in which the capsule 220 is placed. A similar sign may be present on the capsule 220. The signs between the patch 250 and the capsule 220 are preferably identical or symmetrical.

The distinctive signs 272 can be found under the patch 250, on the skin side. Likewise, the signs between the patch 250 and the capsule 220 are preferably identical or symmetrical.

The direction of the arrow can change between the two faces of the patch so that the user visually puts the capsule in the correct direction (i.e. put the microneedles on the skin side of the patch).

Fastening

In order to be able to attach the patch 250 to the casing 120, magnets or ferromagnetic materials 304 may be located in the rigid area 256, preferably evenly around the opening 252.

Patch Kit

Because of its function, the patch 250 has to be changed more often than the capsule. Consequently, it can be provided in several copies, all identical. Alternatively, as the patch 250 must be adapted to the circumstances (skin type, limb size, use conditions), the width and/or the length and/or the properties of the adhesive can be different between two patches of the kit.

In addition, different capsules can be used, with different shapes: the patches can therefore have different orifice 252 shapes.

The invention claimed is:

1. A body monitoring system assembly, comprising:
   a patch for a body monitoring system, the patch comprising a main body with an orifice of at least 2 mm in diameter, the main body comprising a rigid area around the orifice and a flexible area on either side of the rigid area,
   a capsule, the capsule configured to be placed in the orifice of the patch and to be secured thereto, the capsule comprising microneedles configured to be inserted into the skin to sample or analyze a body fluid from the wearer of a body monitoring system when the latter is positioned on a limb of a user, the rigid area of the main body allowing a transmission of the forces received by the patch to the capsule.

2. The assembly according to claim 1, wherein the rigid area has a divisibility line interrupted by the orifice, the divisibility line being configured to allow folding the rigid area of the patch.

3. The assembly according to claim 2, wherein the divisibility line is an axis of symmetry of the orifice.

4. The assembly according to claim 1, wherein the orifice comprises on an inner wall a groove or point recesses, configured to receive the capsule.

5. The assembly according to claim 1, wherein the rigid area has a Shore hardness greater than the flexible area, the two materials being different.

6. The assembly according to claim 5, wherein the Shore hardness of the flexible area is comprised between 20 and 40 and the Shore hardness for the rigid area is comprised between 60 and 80.

7. The assembly according to claim 5, wherein the material of the rigid area is harder than the material of the flexible area.

8. The assembly according to claim 1, wherein the rigid area is at least twice as thick as the flexible area.

9. The assembly according to claim 1, further comprising a planar adhesive substantially covering a planar face of the rigid and flexible areas.

10. The assembly according to claim 9, wherein the adhesive is a silicone-based or an acrylic-based adhesive.

11. The assembly according to claim 9, wherein:
    the main body comprises a plurality of through openings, and
    the adhesive comprises a plurality of through openings,
    the size of the openings of the main body being greater than the size of the openings of the adhesive, and/or the opening area density of the main body is greater than the opening area density of the adhesive, and/or the opening density of the main body is greater than the opening density of the adhesive.

12. The assembly according to claim 11, wherein the flexible area of the main body comprises the plurality of through openings.

13. The assembly according to claim 1, wherein the flexible area comprises a plurality of through openings.

14. The assembly according to claim 1, wherein the rigid area comprises a step having a thickness less than the thickness of the rest of the rigid area.

15. The assembly according to claim 1, wherein the capsule has a thickness identical to the thickness of the rigid area of the main body of the patch.

16. A body monitoring system, intended to be attached to a limb, comprising:
    an assembly according to claim 1,
    a casing, able to be coupled with the capsule, inside which there is a battery and a processor, the processor being configured to process data obtained using the sample or the measurement taken by microneedles,
    a strap, configured to hold the casing in place on the limb, in which the capsule is positioned within the central opening of the patch.

17. A system according to claim 16, wherein the strap or the casing is in contact with the rigid area of the patch, to transmit the forces of the strap to the patch, in order to maintain the penetration of the needles by means of the capsule attached to the rigid area of the main body of the patch.

18. The assembly according to claim 1, wherein the flexible area is all around the rigid area.

19. The assembly according to claim 1, wherein the rigid area is at least three times as thick as the flexible area.

* * * * *